United States Patent [19]

Mazurak et al.

[11] 4,381,782

[45] May 3, 1983

[54] HIGHLY ABSORBENT MATERIALS HAVING GOOD WICKING CHARACTERISTICS WHICH COMPRISE HYDROGEL PARTICLES AND SURFACTANT TREATED FILLER

[75] Inventors: Peter A. Mazurak; Donald M. Fries, both of Outagamie, Wis.

[73] Assignee: Kimberly-Clark Corporation, Neenah, Wis.

[21] Appl. No.: 256,067

[22] Filed: Apr. 21, 1981

[51] Int. Cl.³ .................. A41B 13/02; B32B 5/24; B32B 5/26; B32B 5/30

[52] U.S. Cl. .................. 604/368; 428/283; 428/297; 428/323; 428/403; 604/369; 604/371; 604/375; 604/378

[58] Field of Search .................. 128/287, 288, 290 P; 428/283, 323, 403, 297

[56] References Cited

U.S. PATENT DOCUMENTS

| | | |
|---|---|---|
| 3,005,456 | 10/1961 | Graham . |
| 3,055,369 | 9/1962 | Graham . |
| 3,371,666 | 3/1968 | Lewing . |
| 3,661,815 | 5/1972 | Smith . |
| 3,669,103 | 6/1972 | Harper et al. . |
| 3,900,378 | 8/1975 | Yen et al. . |
| 3,932,322 | 1/1976 | Duchane . |
| 3,997,647 | 12/1976 | Lassen . |
| 4,058,124 | 11/1977 | Yen et al. . |
| 4,059,114 | 11/1977 | Richards . |
| 4,118,531 | 10/1978 | Hauser . |
| 4,174,417 | 11/1979 | Rydell . |

Primary Examiner—James C. Cannon
Attorney, Agent, or Firm—William D. Herrick; R. Jonathan Peters; Howard Olevsky

[57] ABSTRACT

Highly absorbent low density fibrous structures such as webs or batts formed from mixtures of powdered or microcrystalline hydrogel preparations with surfactant treated filler materials having a particle size equal to or greater than the hydrogel particle size. Absorbent materials of the invention exhibit good wicking properties and result in more efficient use of hydrogels by minimizing gel blocking. Additional improvements include reduced dusting, improved stabilization and somewhat higher absorbency when compared with hydrogel materials alone. Uses for these materials include, by way of example and not limitation, disposable diapers, incontinent pads, sanitary napkins, wipes, surgical sponges and the like.

13 Claims, 4 Drawing Figures

AUTOMATED DEMAND ABSORBENCY TEST RESULTS FOR HYDROGELS

HIGHLY ABSORBENT MATERIALS HAVING GOOD WICKING CHARACTERISTICS WHICH COMPRISE HYDROGEL PARTICLES AND SURFACTANT TREATED FILLER

BACKGROUND OF THE INVENTION

1. Field of the Invention

This invention relates to highly absorbent fibrous structures such as webs and batts as well as to methods and compositions for making them. More specifically, it pertains to such fibrous structures including hydrogel or, so-called "superabsorbent" materials. These materials exhibit the ability to absorb many times their weight in aqueous and other liquids making them extremely useful for applications such as disposable diapers, catamenial devices, wipes, surgical sponges and the like. When used alone or in combination with other materials, such hydrogels may permit the absorbing device to be reduced in size for a given application or increase its capacity in use. In most cases, however, to effectively utilize such hydrogels, it is necessary for some means or treatment to be provided to increase contact with the liquid being absorbed by improving distribution of the liquid throughout the absorbing medium. This invention is directed to improvements in achieving such distribution and effective utilization of hydrogel absorbing materials.

DESCRIPTION OF THE PRIOR ART

Hydrogel materials or so-called "super-absorbents" have been known for many years. Examples include lightly crosslinked polymers as described in U.S. Pat. No. 3,669,103 to Harper et al; starch grafted materials such as polyacrylonitrile grafted starch copolymers described in U.S. Pat. No. 3,661,815 to Smith; and a wide variety of chemically treated cellulose materials. In general the cellulose materials may be treated by chemical substitution, etherization or esterification with or without crosslinking and by polymeric grafting. Such materials are described in further detail in U.S. Pat. No. 3,997,647 to Lassen and others. These materials are manufactured in various forms including powders, granules, fibers, and paperlike sheets. Webs may be formed from these materials and are also described in U.S. Pat. No. 3,997,647 to Lassen as well as U.S. Pat. No. 4,174,417 to Rydell.

Effective utilization of such materials has been hindered however, by a phenomenon referred to commonly as "gel-blocking". This describes the tendency of hydrogel materials to swell in place when wetted and produce gelatinous material which blocks further transfer of the liquid being absorbed. Thus, in many cases contact of absorbent material with the liquid being absorbed is highly localized and much of the absorbent medium is not utilized at all. In addition, such hydrogels have proved extremely difficult to handle in bulk form (due to blocking, caking, or dusting) or are otherwise unable to be evenly distributed in a free-flowing manner.

Attempts in the past to solve these problems have been successful only to a limited degree. For example, U.S. Pat. No. 3,932,322 to Duchane relates to mixtures of such hydrogels with fumed silica or alumina fillers to provide increased absorbency. The presence of these fillers in products such as sanitary napkins may be objectionable, and handling during processing results in increased problems of dusting and the like. Mixtures of hydrogels with other materials including cotton, cellulose fibers, and synthetic fibers has been taught. For example, U.S. Pat. No. 3,055,369 to Grahm, Jr. discloses such mixtures for applications including tampon devices. However, such mixtures have not demonstrated satisfactory wicking properties for effective use in connection with fluids such as urine.

SUMMARY

The present invention provides improved highly absorbent hydrogel materials having good wicking properties which are also more stable and easily handled with reduced problems of dusting and blocking. In accordance with the invention the hydrogel materials are mixed with up to 90 percent by weight of a surfactant treated filler material. The resulting material has a reduced tendency to create dusting and is free flowing and easily incorporated into an absorbent device such as a disposable diaper, catamenial device or wiper. Preferred hydrogel materials include carboxymethyl cellulose, polyacrylonitrile grafted starches, as well as entirely synthetic Permasorb-10 (National Starch and Chemical Company). Preferred filler materials include shredded polystyrene, polyethylene, polypropylene or blends of such synthetic materials each of which is treated with a surfactant, preferably Aerosol OT (American Cyanamid) up to a level of about 0.5 percent by weight. The filler material has a relatively large average particle size in the range generally of 1 to 10,000, preferably 1 to 1,000, and, most preferred 10 to 100 times the hydrogel particle size. The resulting material may be incorporated into products by spreading the mixture directly or by forming a web or batt of the mixture and combining the web or batt as a component of the product.

Absorbency and wicking properties of materials of the invention may be controlled within wide limits by varying the composition and relative amounts of hydrogel and filler materials. In general, however, when compared with other hydrogel compositions, materials of the present invention demonstrate improved wicking and absorbency properties. Also, materials of the invention have improved integrity and better mechanical properties which also improve overall in-use absorbent performance.

DESCRIPTION OF THE PREFERRED EMBODIMENTS

Figure 1:
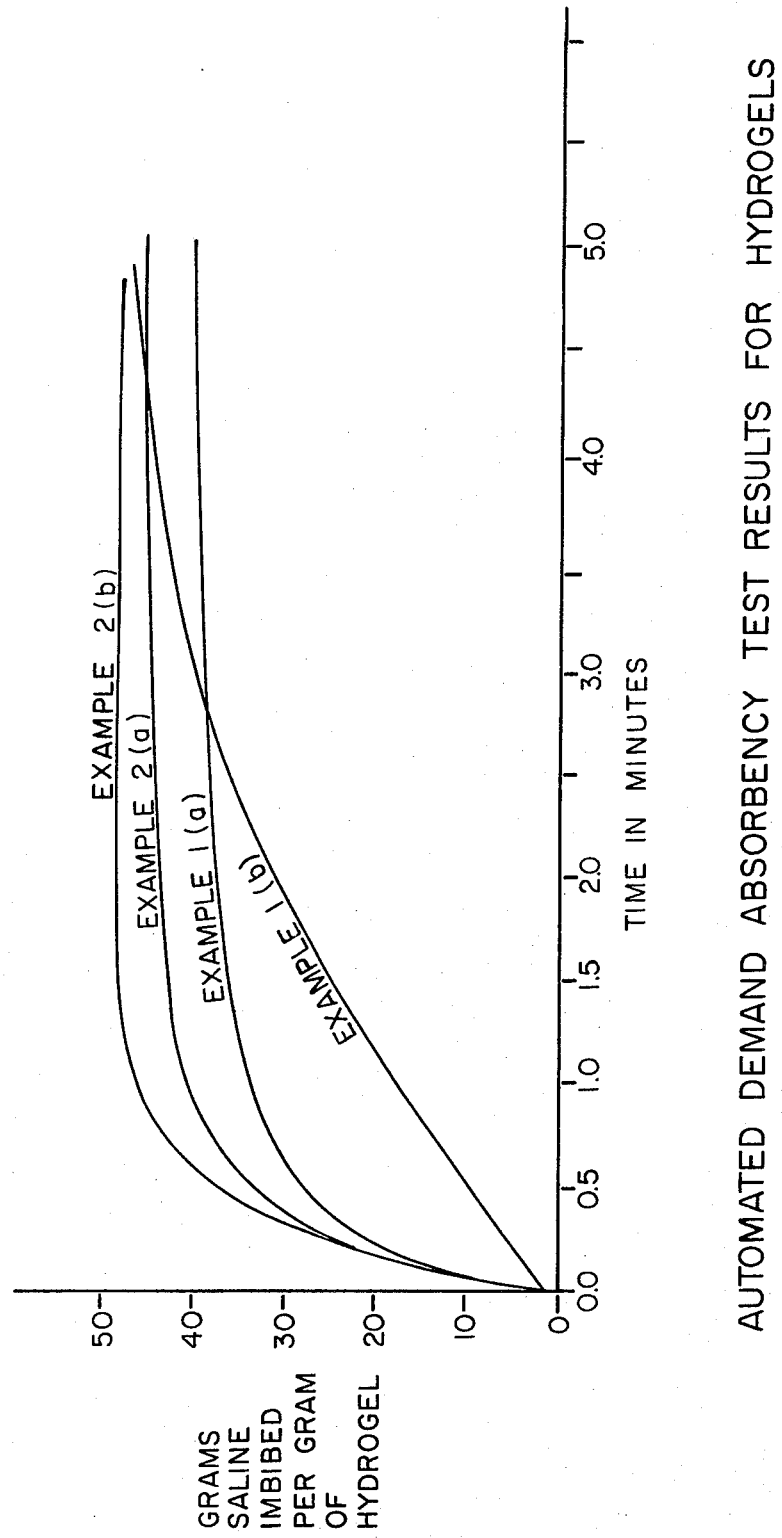
FIG. 1 is a graph illustrating improved absorbency results obtained by means of the present invention.

As used herein the term "hydrogel" refers to dry, solid, water swellable, water insoluble absorbent compositions of polymeric materials capable of absorbing at least 15 times their own weight of body exudate or 1% saline solution. More particularly, such compositions provide gelatinous agglomerates of liquid swollen, particulate members in the presence of body exudate or 1% saline solution. Hydrogels may be initially in powdered or microcrystalline form and prepared by known processes, such as described in U.S. Pat. No. 3,929,741 to Laskey, and U.S. Pat. No. 3,900,378 to Yen et al, for example.

The "filler materials" include a wide variety of materials in powder, fiber, or particulate form which are normally hydrophilic or hydrophobic but may be treated with a surfactant to improve surface wettability. Examples include polyolefins such as polyethylene, polypropylene, and polystyrene, as well as natural, slightly absorbent clays, micas or vegetable (e.g. corn cob) debris, as well as blends of these materials.

Surfactants which may be utilized in accordance with the invention include ionic and nonionic materials such as Aersol O.T. (American Cyanamid), Teepol 610 (Particle Data Laboratories, Ltd.), Neodol-27 (Shell Chemical Company), and Duomeen-361 (Armour Industrial Chemical Company).

To prepare the material of the present invention the filler material is first uniformly wetted with up to about 20 percent by weight of surfactant solution containing surfactant in the range of from about 0.5% to 2.5% by weight. The hydrogel powder is then added and the admixture thoroughly blended to provide an intimate mixture and integration throughout of the components. The hydrogel particles will swell slightly and adhere to the filler material. After drying, the admixture is preferably subjected to slight mechanical action destroying lumps. In use the filler material acts to rapidly wick liquid throughout the mixture and substantially eliminate the tendency to form gel blocks. While it is not desired to limit the invention to any particular theory, it is believed that the surfactant liquid slightly swells the dry hydrogel making it sticky and allowing it to adhere to filler particles. For this reason it is preferred that the filler be damp, including, up to 10% by weight of water prior to mixing with surfactant solution.

The final admixture may be dried or allowed to retain up to 10% by weight of water. Retained moisture prevents formation of hard lumps and also reduces drying costs.

Preferred amounts of filler material are in the range of 5% to 95% and, more preferably, 25% to 75%, based on the weight of hydrogel material with a 50-50 mixture being most preferred. The surfactant is preferably added to filler material in an amount of about 0.05% to 0.5% and, more preferably, 0.1% to 0.2% by weight based on the amount of nonabsorbent filler. The filler material is of relatively large average particle diameter, in the range of from 1 to 10,000 preferably 1 to 1,000, and, most preferred, 10 to 100 times the average hydrogel particle diameter.

The mixture may be collected into a batt prior to drying in which case it is preferably maintained in a uncompressed state with a density in the range of from about 0.05 to 0.25 g/cc, or it may be stored as a particulate mixture having a density of about 0.05 to 0.50 g/cc. As a web or batt of course, it may be used directly as a component of an absorbent product.

The following examples are provided as illustrations of the present invention. Absorbency test results were determined by total immersion of absorbent in test fluid for a period of 2 minutes, allowing nonabsorbed fluid to drain off for a period of 5 minutes, and weighing. Wicking tests were determined by a demand absorbency device as described by Lichstein in pages 129-142 of The INDA Technological Symposium proceedings, March 1974. This equipment was modified by application of a Mettler PL1200 electronic balance which provided a continuous plot of amount of fluid wicked. Density was measured by weight and volume.

EXAMPLE 1

Five hydrogel compositions were obtained and tested individually for absorbency: Polymer 35-A-100 and 35-A-200 (both polyacrylonitrile grafted starch—Grain Processing Corporation), Permasorb 10 (100% synthetic material from acrylic acid precursors—National Starch and Chemical Company), Sanwet IM-300 (polyacrylic acid grafted starch—Sanyo Chemical Corporation), and Stasorb-372 (polyacrylic acid grafted starch—A. E. Staley Chemical Corporation).

EXAMPLE 2

Four of the hydrogels of Example 1 were mixed 50-50 with ground mixture (60/40 weight %) of shredded polyethylene sheet and polypropylene fibers, average particle diameter 1.5 mm, including 0.5% by weight of Aerosol-OT surfactant and tested for absorbency with synthetic urine (1.6% urea in water, surface tension adjusted with surfactant to 55 dynes/cm).

EXAMPLE 3

Using Permasorb 10 and Polymer 35-A-100 as the hydrogel materials, Example 2 was repeated substituting the following as filler materials:
shredded polyethylene (average particle diameter 10 mm), ground corn cobs (average particle diameter 2.5 mm), filler of Example 2 (including 50% pulp fibers average particle size 3.0×0.1 mm), and shredded polystyrene packing material (average particle diameter 1.5 mm).

EXAMPLE 4

Using Permasorb 10 and Polymer 35-A-100 as the hydrogel materials, Example 2 was repeated substituting the following as surfactants: Teepol-610 (anionic secondary alkyl sulfate), Duoment (cationic N-Tallow-proplyenediamine), Neodol 25-7 (nonionic primary alcohol exthoxylate), Aerosol-OT (anionic dioctyl sulfocuccinate).

EXAMPLE 5

Using Permasorb 10 and Polymer 35-A-100 as the hydrogel materials, Example 2 was repeated at the following levels of surfactant (Aerosol O.T.) addon: 0%, 0.1%, 0.2%, 0.3%, 0.4%, and 0.5%.

EXAMPLE 6

Using Permasorb 10 and Polymer 35-A-100 as the hydrogel materials, Example 2 was repeated at a surfactant addition level of 0.25% (Aerosol-OT) based on filler weight and filler to hydrogel ratios as follows: 1/0, 3/1, 1/1, 1/3, 0/1.

EXAMPLE 7

Using Permasorb 10 and Polymer 35-A-100 as the hydrogel materials, Example 2 was repeated at a surfactant (Aerosol-OT) addition level of 0.25% based on filler weight and tested in the following fluids: 0.9% saline, synthetic urine of Example 2, synthetic urine #2 (urea plus mixture of salts including NaCl, $CaCl_2$, $MgCl_2$, $Na_2SO_4$ and $Na_3PO_4$), distilled water and tap water.

EXAMPLE 8

Example 2 was repeated using Polymer 35-A-100 and Permasorb-10 as hydrogels, with 0.25% Aerosol-OT surfactant. Ground corn cob material of several different particle diameter ranges was used as filler material. The Table demonstrates that, as the filler particle diameter increased absorbency was increased as was bulk. For these reasons, filler particle diameters of 1 to 10,000 are preferred with particular preference for diameters within the range of 1 to 1,000 and, especially, 10 to 100 times the hydrogel particle diameter which is generally in the range of from 0.01 mm to 1.0 mm.

The results obtained are illustrated in the Table which shows a marked increase in absorbency obtained by means of the present invention.

TABLE I

| Example | Hydrogel | Filler | Surfactant (Level) | Ratio Filler to Hydrogel | | Absorbency Grams Fluid/ Grams Hydrogel |
|---|---|---|---|---|---|---|
| 1(a) | Permasorb 10 | none | — | — | | 36.5 |
| (b) | Polymer 35-A-100 | none | — | — | | 36.9 |
| (c) | Polymer 35-A-200 | none | — | — | | 32.3 |
| (d) | Sanwet IM-300 | none | — | — | | 47.9 |
| (e) | Stasorb 372 | none | — | — | | 28.3 |
| 2(a) | Permasorb 10 | *PE/PP | 0.5% (Aerosol OT) | 1/1 | | 98.5 |
| (b) | Polymer 35-A-100 | *PE/PP | 0.5% (Aerosol OT) | 1/1 | | 90.3 |
| (c) | Polymer 35-A-200 | *PE/PP | 0.5% (Aerosol OT) | 1/1 | | 97.0 |
| (d) | Stanwet IM-300 | *PE/PP | 0.5% (Aerosol OT) | 1/1 | | 94.7 |
| (e) | Stasorb 372 | *PE/PP | 0.5% (Aerosol OT) | 1/1 | | 51.4 |
| 3(a) | Permasorb 10 | Shredded Polyethylene | 0.5% (Aerosol OT) | 1/1 | | 91.3 |
| (b) | Permasorb 10 | Ground Corn Cobs | 0.5% (Aerosol OT) | 1/1 | | 102.7 |
| (c) | Permasorb 10 | Reclaimed Diapers | 0.5% (Aerosol OT) | 1/1 | | 82.2 |
| (d) | Permasorb 10 | Shredded Polystyrene | 0.5% (Aerosol OT) | 1/1 | | 108.3 |
| (e) | Polymer 35-A-100 | Shredded Polyethylene | 0.5% (Aerosol OT) | 1/1 | | 37.6 |
| (f) | Polymer 35-A-100 | Ground Corn Cobs | 0.5% (Aerosol OT) | 1/1 | | 95.7 |
| (g) | Polymer 35-A-100 | Reclaimed Diapers | 0.5% (Aerosol OT) | 1/1 | | 63.8 |
| (h) | Polymer 35-A-100 | Shredded Polystyrene | 0.5% (Aerosol OT) | 1/1 | | 90.8 |
| 4(a) | Permasorb 10 | *PE/PP | 0.5% (Teepol-anionic) | 1/1 | | 80.8 |
| (b) | Permasorb 10 | *PE/PP | 0.5% (Duoment-cationic) | 1/1 | | 70.0 |
| (c) | Permasorb 10 | *PE/PP | 0.5% (Neodol-nonionic) | 1/1 | | 82.5 |
| (d) | Polymer 35-A-100 | *PE/PP | 0.5% (Teepol-anionic) | 1/1 | | 65.2 |
| (e) | Polymer 35-A-100 | *PE/PP | 0.5% (Duoment-cationic) | 1/1 | | 50.8 |
| (f) | Polymer 35-A-100 | *PE/PP | 0.5% (Neodol-nonionic) | 1/1 | | 64.4 |
| 5(a) | Permasorb 10 | *PE/PP | 0% (Aerosol OT) | 1/1 | | 78.9 |
| (b) | Permasorb 10 | *PE/PP | 0.1% (Aerosol OT) | 1/1 | | 99.7 |
| (c) | Permasorb 10 | *PE/PP | 0.2% (Aerosol OT) | 1/1 | | 90.3 |
| (d) | Permasorb 10 | *PE/PP | 0.3% (Aerosol OT) | 1/1 | | 100.0 |
| (e) | Permasorb 10 | *PE/PP | 0.4% (Aerosol OT) | 1/1 | | 91.4 |
| (f) | Permasorb 10 | *PE/PP | 0.5% (Aerosol OT) | 1/1 | | 102.9 |
| (g) | Polymer 35-A-100 | *PE/PP | 0% (Aerosol OT) | 1/1 | | 66.5 |
| (h) | Polymer 35-A-100 | *PE/PP | 0.1% (Aerosol OT) | 1/1 | | 76.4 |
| (i) | Polymer 35-A-100 | *PE/PP | 0.2% (Aerosol OT) | 1/1 | | 81.8 |
| (j) | Polymer 35-A-100 | *PE/PP | 0.3% (Aerosol OT) | 1/1 | | 81.3 |
| (k) | Polymer 35-A-100 | *PE/PP | 0.4% (Aerosol OT) | 1/1 | | 81.7 |
| (l) | Polymer 35-A-100 | *PE/PP | 0.5% (Aerosol OT) | 1/1 | | 79.4 |
| 6(a) | Permasorb 10 | *PE/PP | 0.25% (Aerosol OT) | 0 | | 0.82 |
| (b) | Permasorb 10 | *PE/PP | 0.25% (Aerosol OT) | 3/1 | | 23.4 (93.7**) |
| (c) | Permasorb 10 | *PE/PP | 0.25% (Aerosol OT) | 1/1 | | 52.5 (105.0**) |
| (d) | Permasorb 10 | *PE/PP | 0.25% (Aerosol OT) | 1/3 | | 56.1 (74.8**) |
| (e) | Permasorb 10 | *PE/PP | 0.25% (Aerosol OT) | 100% Hydrogel | | 36.5 (36.5**) |
| (f) | Polymer 35-A-100 | *PE/PP | 0.25% (Aerosol OT) | 0 | | 0.82 |
| (g) | Polymer 35-A-100 | *PE/PP | 0.25% (Aerosol OT) | 3/1 | | 21.5 (86.1**) |
| (h) | Polymer 35-A-100 | *PE/PP | 0.25% (Aerosol OT) | 1/1 | | 45.2 (90.3**) |
| (i) | Polymer 35-A-100 | *PE/PP | 0.25% (Aerosol OT) | 1/3 | | 34.1 (45.3**) |
| (j) | Polymer 35-A-100 | *PE/PP | 0.25% (Aerosol OT) | 100% Hydrogel | | 36.9 (36.9**) |
| 7(a) | Permasorb 10 | *PE/PP | 0.25% (Aerosol OT) | 1/1 | 0.9% Saline | 37.8 (g/g polymer) |
| (b) | Permasorb 10 | *PE/PP | 0.25% (Aerosol OT) | 1/1 | Synthetic Urine #1 | 98.5 (g/g polymer) |
| (c) | Permasorb 10 | *PE/PP | 0.25% (Aerosol OT) | 1/1 | Synthetic Urine #2 | 37.5 (g/g polymer) |
| (d) | Permasorb 10 | *PE/PP | 0.25% (Aerosol OT) | 1/1 | Distilled Water | 169 (g/g polymer) |
| (e) | Permasorb 10 | *PE/PP | 0.25% (Aerosol OT) | 1/1 | Tap Water*** | 112 (g/g polymer) |
| (f) | Polymer 35-A-100 | *PE/PP | 0.25% (Aerosol OT) | 1/1 | 0.9% Saline | 39.8 (g/g polymer) |
| (g) | Polymer 35-A-100 | *PE/PP | 0.25% (Aerosol OT) | 1/1 | Synthetic Urine #1 | 90.3 (g/g polymer) |
| (h) | Polymer 35-A-100 | *PE/PP | 0.25% (Aerosol OT) | 1/1 | Synthetic Urine #2 | 33.6 (g/g polymer) |
| (i) | Polymer 35-A-100 | *PE/PP | 0.25% (Aerosol OT) | 1/1 | Distilled Water | 89.1 (g/g polymer) |
| (j) | Polymer 35-A-100 | *PE/PP | 0.25% (Aerosol OT) | 1/1 | Tap Water*** | 80.3 (g/g polymer) |
| (k) | Permasorb 10 | none | — | — | 0.9% Saline | 33.3 (g/g polymer) |
| (l) | Permasorb 10 | none | — | — | Synthetic Urine #1 | 36.5 (g/g polymer) |
| (m) | Permasorb 10 | none | — | — | Synthetic Urine #2 | 33.4 (g/g polymer) |
| (n) | Permasorb 10 | none | — | — | Distilled Water | 91.9 (g/g polymer) |
| (o) | Permasorb 10 | none | — | — | Tap Water*** | 100 (g/g polymer) |
| (p) | Polymer 35-A-100 | none | — | — | 0.9% Saline | 33.3 (g/g polymer) |
| (q) | Polymer 35-A-100 | none | — | — | Synthetic Urine #1 | 36.9 (g/g polymer) |
| (r) | Polymer 35-A-100 | none | — | — | Synthetic Urine #2 | 27.0 (g/g polymer) |
| (s) | Polymer 35-A-100 | none | — | — | Distilled Water | 101 (g/g polymer) |
| (t) | Polymer 35-A-100 | none | — | — | Tap Water*** | 75.9 (g/g polymer) |

Ratio Filler

TABLE I-continued

| Example | Hydrogel | (Filler) Particle Size | Surfactant (Level) | to Hydrogel | Absorbency g/g | Bulk ml/g |
|---|---|---|---|---|---|---|
| 8(a) | Polymer 35-A-100 | 0.35 | 0 | 0 | 36.9 | 2.8 |
| (b) | Polymer 35-A-100 | 3.69 | 0.25% (Aerosol OT) | 1/1 | 95.7 | 7.2 |
| (c) | Polymer 35-A-100 | 1.35 | 0.25% (Aerosol OT) | 1/1 | 66.3 | 4.7 |
| (d) | Polymer 35-A-100 | 0.54 | 0.25% (Aerosol OT) | 1/1 | 55.0 | 4.3 |
| (e) | Polymer 35-A-100 | 0.43 | 0.25% (Aerosol OT) | 1/1 | 30.8 | 4.2 |
| (f) | Permasorb 10 | 0.49 | 0 | 0 | 36.5 | 2.7 |
| (g) | Permasorb 10 | 3.69 | 0.25% (Aerosol OT) | 1/1 | 102.7 | 6.6 |
| (h) | Permasorb 10 | 1.35 | 0.25% (Aerosol OT) | 1/1 | 92.0 | 4.3 |
| (i) | Permasorb 10 | 0.54 | 0.25% (Aerosol OT) | 1/1 | 35.6 | 4.0 |
| (j) | Permasorb 10 | 0.43 | 0.25% (Aerosol OT) | 1/1 | 31.8 | 3.9 |

*Mixture of shredded polyethylene film and polypropylene fibers (60:40 w/w).
**Per gram polymer present.
***Town of Menasha, Wisconsin FIG. 1 is a graph of automated demand absorbency test results showing increased wicking performance resulting from the present invention. As shown, the wicking performance of hydrogel absorbents is increased greatly through incorporation with fillers.

Figure 2:
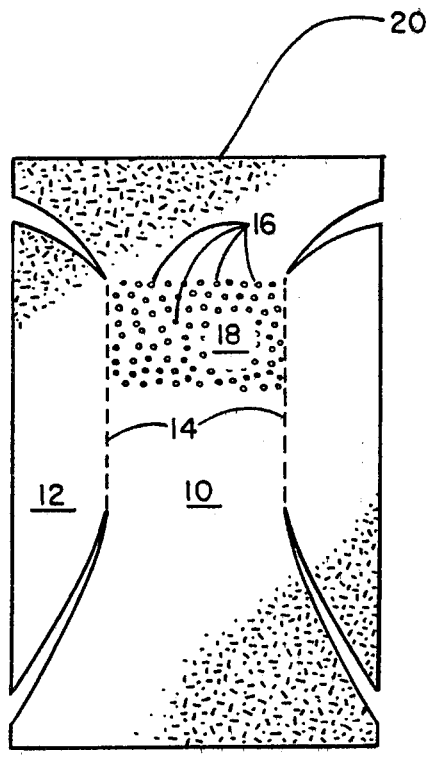
FIGS. 2, 3 and 4 illustrate the present invention in the form of a disposable diaper.
Figure 3:
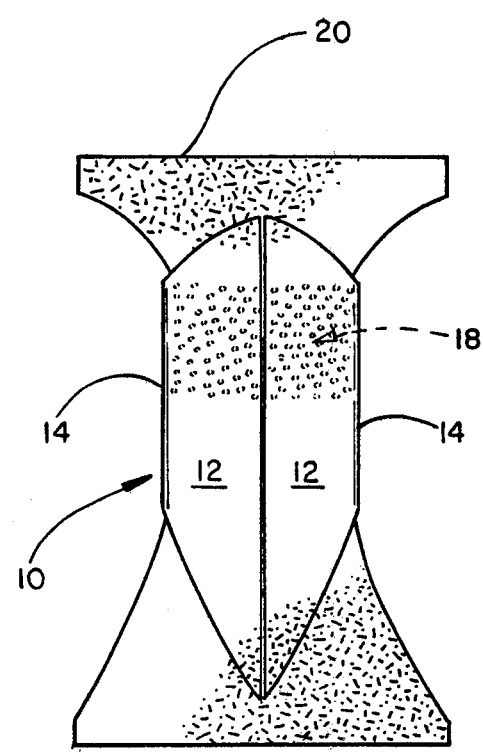
Figure 4:
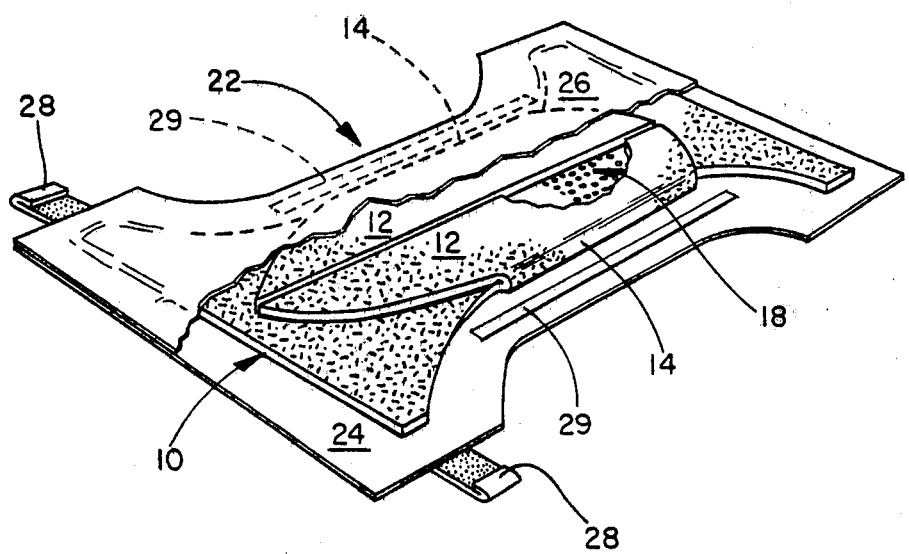

Turning to FIGS. 2 through 4, a preferred disposable sanitary garment application for the material of the present invention will be described. FIGS. 2 and 3 show the absorbent layer, 10, prior to incorporation into the diaper. Cutout areas 12 provide for folding along lines 14. Prior to folding, hydrogel material 16 is incorporated by placement at 18 near the front edge 20 of batt 10. After folding, the batt 10 may be incorporated into diaper 22 as shown in FIG. 4. Diaper 22 also includes liquid impermeable backing 24 and permeable liner 26 as well as fastening means 28. Elastic means 29 are provided to aid in fluid retention within the diaper structure. While the amount of hydrogel material 16 may vary within a wide range, useful results have been obtained with amounts in the range of from about 1 gm to 10 gm distributed evenly in area 18 as illustrated. The liner 26 may be a nonwoven material such as spunbonded polypropylene, carded webs, or the like or a split or fibrillated film. The backing 24 may be any of a wide variety of films such as matt embossed polyethylene, for example. Fastening means 28 may be adhesive tabs, for example. Other variations will also be useful and suggest themselves to those skilled in the art such as shape modifications, reinforcement of stress areas, and incorporation of elastic. These variations can also take advantage of the hydrogel configuration of the present invention. An advantage will be in reduced fluff requirements.

In a specific example, a diaper was prepared as in FIGS. 2 through 4 using 22 grams of fluff instead of the normal 36 grams used for that size of standard product. To that fluff was added 3 grams of the hydrogel admixture of Example 1 as shown in FIGS. 2 and 3. The resulting product performed as well as the standard diaper in terms of leakage resistance.

As demonstrated above, the present invention provides a more effective use of highly absorbent materials that can be more easily incorporated into end uses such as catamenial devices, disposable diapers, incontinent pads, wipes and the like. While the invention has been described in conjunction with specific embodiments thereof, it is evident that many alternatives, modifications and variations would be apparent to those skilled in the art in light of the foregoing description. Accordingly, it is intended to embrace all such alternatives, modifications and variations as fall within the spirit and broad scope of the appended claims.

We claim:

1. A low density highly absorbent material having improved wicking characteristics comprising an intimate mixture of particulate hydrogel material with 5 to 95 percent by weight of a filler material, said filler material having an average particle diameter 1 to 10,000 times the average hydrogel particle diameter and having been treated with a surfactant.

2. The material of claim 1 wherein the surfactant is anionic dioctyl sulfosuccinate.

3. The material of claim 2 wherein the average filler particle diameter is 1 to 1,000 times the average hydrogel particle diameter.

4. The material of claim 2 wherein the average filler particle diameter is 10 to 100 times the average hydrogel particle diameter.

5. The material of claim 2 wherein the filler is selected from the group consisting of mixtures of polyethylene sheet and polypropylene fibers, ground vegetable debries, mixtures of polypropylene fibers and pulp fibers, and shredded polystyrene.

6. The material of claim 2 wherein the amount of filler is in the range of 25 to 75% based on the weight of hydrogel.

7. The material of claim 2 in batt form having a density in the range of from 0.05 to 0.50 g/cc.

8. The material of claim 1 wherein the surfactant is added at a level of up to about 1.0 percent by weight remaining on the material after drying.

9. A disposable sanitary garment comprising, in combination:
   (a) a liquid impermeable backing,
   (b) a liquid permeable liner, and
   (c) between said backing and said liner an absorbent layer comprising a low density, highly absorbent material having improved wicking characteristics comprising an intimate mixture of particulate hydrogel material with 5 to 95% by weight of a filler material, said filler material having an average particle diameter 1 to 10,000 times the average hydrogel particle diameter and having been treated with a surfactant.

10. The disposable sanitary garment of claim 9 in the form of a disposable diaper wherein the absorbent layer includes said low density material placed near the front edge thereof and the sides of the absorbent layer are folded over covering said low density material.

11. The disposable diaper of claim 10 wherein the hydrogel material contains filler having an average particle diameter 10 to 100 times the average hydrogel particle diameter and wherein said surfactant is anionic dioctyl sulfosuccinate.

12. The disposable diaper of claim 11 further including elastic means to aid in fluid retention.

13. The garment of claim 9 wherein the surfactant is added at a level of up to about 1.0 percent by weight remaining on the material after drying.

* * * * *